US011413095B2

(12) United States Patent
Hladio et al.

(10) Patent No.: US 11,413,095 B2
(45) Date of Patent: Aug. 16, 2022

(54) SYSTEM AND METHOD FOR SURGICAL PLANNING

(71) Applicant: INTELLIJOINT SURGICAL INC., Waterloo (CA)

(72) Inventors: Andre Novomir Hladio, Waterloo (CA); Richard Tyler Fanson, Stoney Creek (CA); Kevin Morency, Guelph (CA); William Halford, Waterloo (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 935 days.

(21) Appl. No.: 16/177,948

(22) Filed: Nov. 1, 2018

(65) Prior Publication Data

US 2019/0133695 A1 May 9, 2019

Related U.S. Application Data

(60) Provisional application No. 62/581,307, filed on Nov. 3, 2017.

(51) Int. Cl.
*A61B 34/20* (2016.01)
*A61B 5/06* (2006.01)
(Continued)

(52) U.S. Cl.
CPC ............. *A61B 34/20* (2016.02); *A61B 5/064* (2013.01); *A61B 5/066* (2013.01); *A61B 5/4851* (2013.01); *A61B 5/4887* (2013.01); *A61B 5/7425* (2013.01); *A61B 2034/105* (2016.02); *A61B 2034/2057* (2016.02); *A61B 2034/2065* (2016.02); *A61B 2034/2068* (2016.02);
(Continued)

(58) Field of Classification Search
CPC .......... A61B 2017/00203; A61B 2017/00207; A61B 2034/105; A61B 2034/2055; A61B 2034/2057; A61B 2034/2065; A61B 2034/2068; A61B 2090/364; A61B 2090/372; A61B 2090/373; A61B 2090/502; A61B 2576/02; A61B 34/10; A61B 34/20; A61B 34/25; A61B 5/064; A61B 5/066; A61B 5/4851; A61B 5/4887; A61B 5/7425; G16H 30/40
See application file for complete search history.

(56) References Cited

U.S. PATENT DOCUMENTS

| | | | |
|---|---|---|---|
| 2005/0043837 A1* | 2/2005 | Rubbert | A61C 7/00 700/98 |
| 2007/0078678 A1* | 4/2007 | DiSilvestro | A61B 34/20 705/2 |
| 2016/0015465 A1* | 1/2016 | Steines | A61B 17/17 623/18.11 |

* cited by examiner

*Primary Examiner* — Michael T Rozanski

(57) ABSTRACT

A system and method perform a registration such as for a surgical navigation system by fitting a plurality of anatomical points as received to a digital model and developing a map having a corresponding confidence level indicating a degree of certainty. As additional anatomical points are received, they are continually matched to the digital model and the confidence level continually updated. The confidence level is output in any form, such as a score, a color code, or other metric. The output may include a graphical representation e.g. overlaid on an image from the digital model. The output may be a heat map overlaid on the image. The heat map may indicate an overall confidence level, and/or may indicate a plurality of confidence levels at various locations on the digital model. The overlay may provide an indication as to one or more suggested probe points to increase the level.

22 Claims, 8 Drawing Sheets

(51) Int. Cl.
  *A61B 5/00* (2006.01)
  *A61B 90/00* (2016.01)
  *A61B 34/10* (2016.01)
(52) U.S. Cl.
  CPC ... *A61B 2090/364* (2016.02); *A61B 2090/373* (2016.02); *A61B 2576/02* (2013.01)

SYSTEM AND METHOD FOR SURGICAL PLANNING

CROSS-REFERENCE

This application claims, in respect of the United States, the domestic benefit of, and in respect of other jurisdictions, Paris convention priority to U.S. Provisional Application No. 62/581,307 filed Nov. 3, 2017 and entitled "System and Method for Surgical Planning" and the contents of this application is incorporated herein by reference in its entirety in respect of any jurisdiction where such incorporation is permitted.

FIELD

The present application relates to computing and to computer assisted procedures and, more particularly, to a system and method for surgical planning such as prior to a surgical procedure using a surgical navigational guidance system.

BACKGROUND

In Total Joint Arthroplasty (TJA), such as Total Hip Arthroplasty (THA) or Total Knee Arthroplasty (TKA), a surgeon may use a navigation system to assist in the surgery. Navigation systems may include computer guided systems that indicate to the surgeon relevant (and possibly relative) locations of the patient, portions of the patient anatomy, surgical devices/prostheses, surgical tools, etc. Navigation systems often require that a patient be registered with one or more digital models of the patient. Registered means, broadly, having defined a relationship/mapping between a representation of the patient (e.g. a portion of the patient's anatomy) in the digital model and anatomical data (spatial data) for the patient as generated before or during a procedure using a surgical navigation system. Existing registration methods may often require that a surgeon physically locate and touch several dozen anatomical points on a patient anatomy to provide the anatomical data to a computer system, which then fits the anatomical points to the digital model to define the relationship/mapping. A problem with traditional methods is that the surgeon will often input a myriad of points (e.g. by touching probe to the patient anatomy of interest) and the system may still not be able to precisely register the patient with the digital model. Additionally, the surgeon may spend an excessive amount of time probing various areas of a patient anatomy to provide anatomical points.

SUMMARY

There is provided a computer implemented method for a surgical procedure comprising: receiving a digital model identifying at least a portion of a bony structure of a patient anatomy; receiving a plurality of anatomical points identifying actual locations on a patient anatomy; creating a mapping by correlating the plurality of anatomical points to the digital model, wherein the mapping matches received anatomical points with a surface of the bony structure identified in the digital model; determining a confidence level corresponding to a likely correctness of the mapping of the anatomical points to the digital model; presenting a representation of the confidence level; determining, from one or more of the digital model, the anatomical points, and the confidence level, suggested regions from which to obtain additional anatomical points to increase the confidence level of the mapping; presenting the suggested regions; receiving one or more additional anatomical points; updating the mapping by correlating at least a subset of the plurality of anatomical points and the one or more additional anatomical points to the digital model; and updating the confidence level.

Receiving the plurality of anatomical points may comprise determining a location of a tip of a probe for each of the plurality of anatomical points. Receiving the plurality of anatomical points may comprise receiving input from a scanner being manipulated to scan a region of the patient anatomy.

The representation of the confidence level may comprise one or more of a numerical value, a binary value, or a heat map. Presenting the representation of the confidence level may comprise displaying a heat map overlaid over one or more regions of an image generated from the digital model, wherein different areas of the heat map identify varying degrees of confidence. The binary value may identify whether a confidence has reached a predetermined threshold value.

Presenting the suggested regions may comprise presenting a heat map overlaid on a visualization of the digital model wherein the heat map indicates the suggested regions. The suggested regions may be determined, at least in part, to provide an area from which additional anatomical points can be obtained which will increase the confidence level without requiring a high degree of precision to indicate the additional anatomical points.

The confidence level may be updated in at least near real time when an additional anatomical point is received.

There is provided a system for performing patient registration during a medical procedure, comprising: a computer system; a data store; an input system; and a display system. The computer system is configured to: receive a digital model representative of a patient anatomy; receive, from the input system, information identifying a plurality of anatomical points, the anatomical points corresponding to a location of a patient in three-dimensional space; determine a mapping to map the plurality of anatomical points to digital points on the digital model; determine a confidence level associated with the mapping; and determine, one or more suggested areas of a patient anatomy from which to obtain additional anatomical points to increase the confidence level of the mapping.

The computer system may be further configured to output, via the display system, a representation of the confidence level associated with the mapping. The computer system may be further configured to output to the display system a heat map overlaid on an image generated from the digital model, wherein the heat map indicates the suggested areas of a patient anatomy from which additional anatomical points are to be received to improve the confidence level. The computer system may be further configured to receive additional information representative of one or more additional anatomical points to update the confidence level and to update the output of the heat map output to the display system.

The input system may comprise a vision system and a probe, wherein the vision system is configured to view at least a portion of the probe and to determine, based on a geometry of the probe, a position of the probe in three-dimensional space.

The computer system may be further configured to: receive an initial coarse patient registration correlating the location of the patient in three-dimensional space with the digital model; and determine an initial confidence level and one or more suggested areas based on the an initial coarse patient registration.

There is provided a computer-implemented method for identifying anatomical locations associated with a surgical target position. The method comprises: receiving a three-dimensional digital model of a region of a patient anatomy; receiving data representing a surgical target position in a coordinate system of the three-dimensional digital model; determining, based on the three-dimensional digital model and the data representing the surgical target position, three or more locations on the three-dimensional digital model, the locations having a defined spatial relationship with the surgical target position; and providing for display a visualization of the three-dimensional digital model and at least a subset of the three or more locations.

The method may further comprise: generating a respective local region around each of the three or more locations, wherein each respective local region is generated by computing a deviation from the surgical target position by substituting one location of the three or more locations with points within the respective local region; and selecting one respective local region comprising points where the deviation is below an accuracy threshold. The method may further comprise: displaying an indication of the accuracy threshold; receiving a change to the accuracy threshold; and updating each respective local region in real time based on the change to the accuracy threshold.

The method may comprise receiving updated data representing the surgical target position and performing the determining and providing steps in real time in response to update the display of the three-dimensional digital model and the at least the subset of the three or more locations.

The method may further comprise providing the surgical target position for display relative to the three-dimensional digital model. The surgical target position may be represented graphically as a representation of one or more of a prosthesis and an instrument. The prosthesis may be an acetabular component.

The surgical target position may be a plane.

The defined spatial relationship may be a matching relationship, wherein the three or more locations on the three-dimensional digital model form a plane that corresponds to the surgical target position.

The defined spatial relationship may comprise a pose in a known coordinate system. The known coordinate system may be an anatomical coordinate system. The method may further comprise: receiving pose data of actual locations on the patient anatomy corresponding to the locations on the three-dimensional digital model from a localization system; determining the surgical target position with respect to a localization system coordinate frame based on the pose data and the defined spatial relationship; and providing navigational information with respect to the surgical target position. The method may further comprise registering the anatomical coordinate system to the localization system; and the defined spatial relationship may be a pose with respect to the anatomical coordinate system.

The method may further comprise receiving an indication of a type of surgical approach to be used; and determining the three or more locations on the digital model may include determining whether the three or more locations are exposed during a surgery using the indication of the type of surgical approach.

The method may further comprise determining a plurality of sets of locations, wherein each set of the plurality of sets of locations comprises three or more locations on the three-dimensional digital model, and the three or more locations in each set have a defined spatial relationship with the surgical target position that is different from any other set in the plurality of sets of locations.

There is provided a navigation system comprising: an input system; and a computer executing instructions to: receive anatomical points as input from the input system, the anatomical points corresponding to anatomical locations provided for display to a user, and having a defined spatial relationship with a surgical target; access the defined spatial relationship with the surgical target; register the surgical target to the navigation system based on the defined spatial relationship and the anatomical points; and provide navigational information with respect to the surgical target position.

Figure 1A:
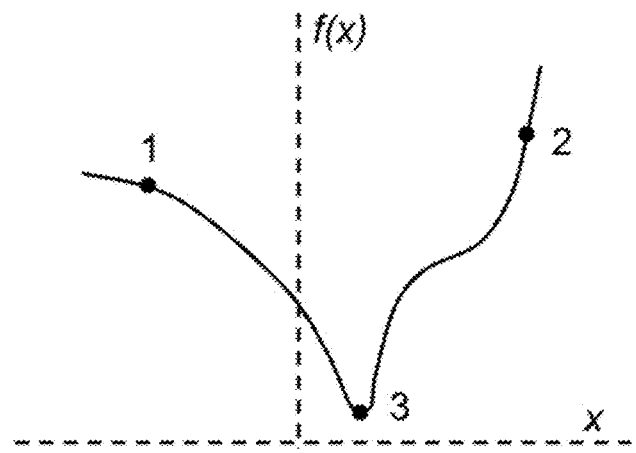
FIGS. 1A, 1B and 1C are respective graphs showing respective minimization operations on example functions $f(x)$.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light. Additionally, the word exemplary is used herein to mean, "serving as an example, instance or illustration." Any embodiment of construction, process, design, technique, etc., designated herein as exemplary is not necessarily to be construed as preferred or advantageous over other such embodiments. Particular quality or fitness of the examples indicated herein as exemplary is neither intended nor should be inferred.

DETAILED DESCRIPTION

Methods and devices are provided for use during surgical procedures. The surgical procedures may include Total Joint Arthroplasty (TJA), such as Total Hip Arthroplasty (THA) or Total Knee Arthroplasty (TKA). The methods and devices may include determining a plurality of points on a patient anatomy ("anatomical points") in three-dimensional space, such as by probing or scanning a region of the patient anatomy, and fitting or mapping those points to a digital model of the patient anatomy. In an example, the determination of a plurality of anatomical points may occur before, or during a medical procedure. The digital model of the patient may be retrieved prior to a medical procedure, or during. The digital model may comprise medical images, and may be of any modality where musculoskeletal structures can be visualized in three dimensions. For example, computed tomography (CT) scans, magnetic resonance imaging (MRI) scans, EOS scans (EOS Imaging, Paris, France), etc. The digital model may be in Digital Imaging and Communications in Medicine (DICOM), or any other digital format. All images in the digital model may be of a single modality; alternatively, some images may be of differing modalities. The digital model could be a stereolithography file (an STL file), a file format native to the stereolithography CAD software created by 3D Systems, Inc. based on a segmented 3D volume, where the STL file represents the surface of a patient's bone.

The methods and systems disclosed herein are intended to provide one or more advantages over existing navigation systems. In disclosed systems and methods, as the plurality of anatomical points are received, they are fitted to the digital model in real time or near-real time. As the anatomical points are fitted, the "map" will be developed, and will have a corresponding confidence level, indicating the degree of certainty with which the anatomical points are matched to the digital model. As additional anatomical points are received, they are continually matched to the digital model, and the confidence level continually updated. The system may output an indication to a user of the confidence level. The output to the user may be in any relevant form, such as a numeric confidence level, a color-coded confidence level, or other metric as appropriate. The display to a user may include a graphical representation, and may include a display of the digital model. In one example, the display may provide a graphical view of the digital model, with an overlay. The overlay may include an indication of the mapping of at least a subset of the received anatomical points onto the digital model.

The overlay may indicate a confidence level of the mapping of the plurality of anatomical points to the digital model. The confidence level may be displayed, for example, as a heat map. The heat map may indicate an overall confidence level, and/or may indicate a plurality of confidence levels at various locations on the digital model. The overlay may, additionally or alternatively, provide an indication as to one or more suggested probe points. Suggested probe points may include anatomical points on the patient, indicated on the digital model (e.g. images generated from the digital model), from which additional received anatomical points may increase the confidence level most efficiently and/or most drastically (e.g. maximally). Efficiently may refer, for example, to increasing the confidence level through the addition of the fewest additional anatomical points. For example, certain areas on a patient anatomy may have a shape or contour that would lend itself to being more- or less-identifiable through a variety of anatomical points. A spherical surface, for example, may be identifiable as a sphere through the analysis of a plurality of anatomical points, though the actual position of the spherical surface relative to the rest of the patient anatomy may not be identifiable without probing anatomical points outside the sphere. On the other hand, there may be areas of the patient anatomy which are physically unique, relative to nearby areas of the patient anatomy. These unique areas of the patient anatomy may be more easily distinguished from other areas of the patient anatomy and thus may be more easily identifiable through just a few anatomical points. Determining a confidence level may use various metrics individually or in combination. For example, a confidence level may be determined using the number of anatomical points, the spatial coverage of the anatomical points, the optimization residual of the computation that determines the mapping, etc.

For a given digital model, and plurality of anatomical points, a function $f(x)$ can be defined which represents how well the anatomical points fit the digital model under a given transformation x, also known as a residual. This transformation is multi-variate, and can include parameters related to translation, rotation, and scaling, in 1 or more dimensions. The parameters are not limited to those listed. The process of mapping the plurality of anatomical points to the digital model can be represented as a minimization of the transformation space over the function:

$$\min_x f(x)$$

A minimization can require a starting guess $x_0$ and the process of mapping anatomical points to a digital model using a minimization with a starting guess can be expressed as:

$$g(x_0) = \min_x f(x), \text{ starting at } x_0$$

and represents the result of point-model minimizations over the entire parameter space of starting guesses. The optimization can be said to be well constrained, if for a space of the parameters in $x_0$, $g(x_0)$ converges on the same x, OR if it converges on a different x, but the residual of the minimization is sufficiently large. This is a method of finding a global minimum within an optimization space containing many local minima. The optimization is not well constrained if there are one or more local minima which have a residual close to the global minimum, to some tolerance.

Figure 1B:
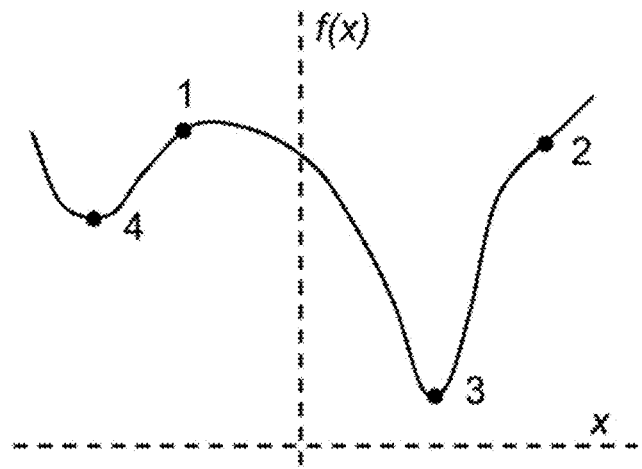
Figure 1C:
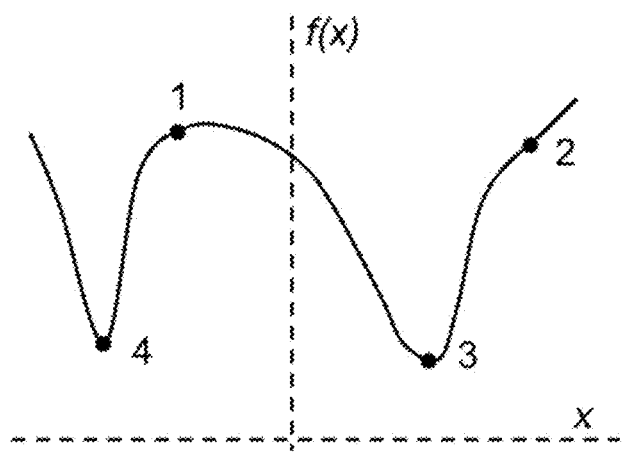

FIGS. 1A, 1B and 1C are graphs illustrating minimizing of example functions $f(x)$. Regarding FIG. 1A, minimizing $f(x)$ by starting at point 1, or point 2, will result in point 3. This is a well-constrained optimization. Regarding FIG. 1B, minimizing $f(x)$ when starting at point 1 results in point 4, but when starting at point 2 results in point 3. However, since the minimization residual at point 4 is much larger than point 3, the overall minimization is still well-defined. Regarding FIG. 1C, minimizing $f(x)$ starting at point 1 results in point 4 again, and when starting at point 2 results in point 3. However, since the minimization residual at point 4 is similar to the residual at point 3, the minimization is not well-defined.

A torus (donut shape) is an example of a geometry that would not be well-constrained. If a plurality of points representing the surface of the torus was mapped to that surface, rotating those points around the axis of the torus would still result in points which were mapped well to the surface.

As indicated, as the system receives additional anatomical points, through probing, scanning, etc., the confidence level may be updated in real time or near real time. The system may include a "goal" or "target" confidence level which, upon being reached, a user may be notified. Once notified, the user may cease to input additional points to the system. By determining a dynamic confidence level, and indicating to a user when the confidence level is achieved, the process of mapping a digital model to the patient anatomy may be accomplished using far fewer anatomical points than traditionally used. This may also have an added benefit of saving time (e.g. during a procedure) in an operating room.

A system employing the above techniques may be incorporated into a broader system for surgical navigation. For example, when the confidence level is at a sufficiently high level that there is assurance that the digital model is appropriately mapped to the physical patient, as outlined by the received points, the mapping may be used to guide surgical instruments relative to the physical patient. In one example, the methods above may be used in TJA to navigate with respect to one or more bones or joints.

A system for implementing the above may comprise a computer, a data source, an input mechanism, and a display mechanism.

In one example, the data source may comprise hardware local to the computer, such as a hard drive, a solid-state drive, or removeable media which may be connected to the computer. In an example, the data source may comprise hardware which is not local to the computer, such as a server or storage device accessible to the computer through a wired or wireless connection. The data source may include storage configured to store one or more digital models of a patient.

The input mechanism is used to provide anatomical points to the computer. The input mechanism may include, for example, a vision system configured to visually identify, directly or indirectly, precise locations of anatomical points on a patient anatomy. The vision system may include, for example, a camera configured to locate the position of a plurality of spheres connected to one end of a probe, the probe having a known geometry such that the computer can accept information related to the position of the spheres and determine the location of a tip of the probe in three-dimensional space. The tip of the probe may be at the end of the probe opposite the spheres. The tip of the probe may then be used to touch anatomical points on a patient anatomy, to provide the computer with the anatomical points for subsequent mapping to a digital model. The vision system may comprise a vision system like the Intellijoint Hip system, aspects of which are identified in U.S. Pat. No. 9,603,671, which is hereby incorporated herein in its entirety. In another example, a vision system may comprise a scanning system, configured to project radiation toward a patient, and collect at least a subset of the projected radiation to thereby determine the location of anatomical points of the patient anatomy relative to the vision system. The at least a subset of the projected radiation may comprise radiation reflected off one or more anatomical structures. In one such example, the scanning system may be a laser system configured to project laser light toward a patient anatomy, an example of which is outlined in WIPO Patent Application No. WO2016065459A1, which is hereby incorporated herein by reference in its entirety.

The vision system may be coupled with the computer system to share data therewith. The data share may be one directional or bi-directional, and may be wired or wireless. The computer may receive the data from the vision system and determine therefrom a three-dimensional representation of the patient, and identify the location of the points in three-dimensional space. The location in three-dimensional space may be relative to axes chosen by the computer.

Upon receiving information from the input system, the information comprising data indicative of a plurality of anatomical points on the patient anatomy, the computer may attempt to match the plurality of anatomical points to locations on the digital model. The plurality of anatomical points may be capable of having a "fit" in more than one location of the digital model. If there are a plurality of locations at which the plurality of points may "fit", each of these locations may be mapped with a respective degree of certainty in each of the plurality of locations. Depending on the number of potential fits, and the level of precision of the respective fit, the computer program may determine a confidence level associated with the correlation. As more anatomical points are gathered through the input system, and provided to the computer, the additional anatomical points are used to refine the mapping to the digital model. As the mapping is refined, one or more of the fits may be eliminated as possible mappings. Moreover, as the mapping is refined, the confidence level will change, and should increase, as more anatomical points are added.

Attempting to match a plurality of points to locations on a digital model may comprise one or more of a coarse registration and a fine registration. A method of coarse registration between a digital image and the anatomical points may be performed by receiving, via the input system, in the computer anatomical points to identify gross anatomical points on the anatomy in a first coordinate frame, receiving input to identify locations on the digital image corresponding to the anatomical points in the digital image coordinate frame, and determining a transformation to map the anatomical points to the identified locations in the respective coordinate systems. After determining a coarse registration, steps to perform a fine registration may follow, in which additional anatomical points are gathered and registered to the digital image coordinate frame. Additional computations may be performed using an initial guess of registration; at least in part to determine a transformation that aligns the digital image data and the received anatomical points with higher accuracy. For example, the computations may be an optimization operation such as iterative close point (ICP), where Euclidean distance between identified points on the digital image and the plurality of anatomical points is minimized, using the coarse registration to define an initial condition for the optimization operation.

The confidence level determined by the computer may be presented to a user via the display. The presentation of the confidence level may include a numerical value, a heat map, and/or other mechanism of conveying the confidence level. In one example, a heat map may be overlaid on an image representative of the digital model of the patient anatomy. The heat map may indicate an overall confidence level, and/or may indicate confidence levels at any of a plurality of points on the digital model. The heat map overlay may also indicate suggested regions or areas for probing or scanning. That is, the map may suggest areas on the patient anatomy which may provide the most efficient means of increasing the confidence level of the mapping. For example, additional anatomical points within a generally-spherical anatomical feature (e.g. a portion of an acetabulum) may not drastically increase the confidence level, if at all, as the geometry of a sphere is consistent throughout and thus the orientation of the anatomical feature in three-dimensional space may not be ascertainable. On the other hand, the anatomy surrounding the acetabulum may define features, such as peaks or valleys along a rim, which are distinct. Mapping these distinct anatomical points may allow the system to increase the confidence of the mapping significantly, with fewer additional anatomical points. See FIGS. 2 and 3 described further below, which show a heat map illustrating the concept, where the areas of the heat map in a lighter shade, around the outside portion of an anatomical feature (in this case, an acetabulum), are areas that may prove more efficient in improving the confidence mapping than the areas in a darker shade which define a spherical surface.

As indicated above, the system may continue to monitor a confidence level of a mapping. The system may be configured to notify a user of the confidence level on an ongoing basis. Additionally, or alternatively, the system may be configured to indicate to a user when the confidence level has reached or exceeded a threshold level, which level may be predetermined. This may be useful in that once the mapping has reached the predetermined threshold confidence level, the user may then cease obtaining additional anatomical points, and may then continue with the next step of a surgical procedure.

The above methods and systems may have significant value in a number of ways. The heat map may serve as a guide to ensure that useful anatomical points are obtained more quickly, and that time is not wasted obtaining additional anatomical points from areas of the patient anatomy that are not going to provide as much utility in identifying the correlation between the digital model and the patient anatomy. The total number of anatomical points required to obtain a high confidence level may be significantly less than the number of anatomical points traditionally gathered during a procedure. This may have the added benefit of reducing the total procedure time, allowing for reduced OR time, and increased throughput.

In one example, a system and method embodying the above may comprise receiving an initial, coarse patient registration and determining an initial mapping based on the coarse registration. This initial registration may have a relatively low confidence level, but may be useful in developing a heat map to display and to thereby guide a user in refining the mapping.

In an example, a method or system may be useful for identifying anatomical locations on a patient which are associated with a surgical target position. Such a method may comprise receiving a digital model of a region of the patient's anatomy, such as a 3D digital representation, from a data store. The method may further comprise receiving data representing a surgical target position, in a coordinate system of the digital model. The data representing a surgical target position may be obtained from a user manually inputting the data, from automated planning software, etc. The obtained surgical target position data may be obtained in a first coordinate system, and subsequently transformed into the coordinate system of the digital model. The surgical target position data, and the digital model representative of the patient anatomy, may subsequently be analyzed to determine one or more locations on the digital model which have a defined spatial relationship with the surgical target position. Alternatively, in an example, one or more locations on the digital model may be chosen and the locations may be analyzed to determine the defined spatial relationship. In one example, the process of determining one or more of the locations on the digital model having a defined spatial relationship may be repeated to provide a series of options to a user, such as a surgeon. The user may choose one of the options, and the associated locations, from the one or more options. The choice of option, and thus the choice of locations having a defined spatial relationship, may be based on the knowledge of the surgeon, such as a preferred surgical method. In another example, particular anatomical regions may be identified prior to the identification of locations on the digital model having a defined spatial relationship. The particular anatomical regions may be identified, for example, by a surgeon with knowledge of the procedure, to ensure the locations with a defined spatial relationship will be accessible during the procedure. Additionally, or alternatively, the particular anatomical region may be identified by a computer attached to the system. For example, a computer may be configured to identify particular anatomical features, such as an acetabulum or femoral head, and use the information in choosing an anatomical region from which to determine the locations having a defined spatial relationship.

The method may further comprise providing for display a visualization of the digital model, as well as the location of the plurality of chosen anatomical points (see FIGS. 2 and 3 described further below). The location of the plurality of chosen anatomical points may be displayed on (e.g. graphically overlaid), with respect to, and/or integrally with the digital model. The display of the anatomical points may comprise displaying the specific anatomical points, or it may comprise displaying a region of interest associated with a particular anatomical point. For example, the display may comprise a local region around each point of a plurality of anatomical points. In an example, the local region may be generated by computing the deviation from the surgical target position, by substituting the location with points within the local region, and selecting a region comprising points where the deviation is below an accuracy threshold. Providing a region of interest, as opposed to simply a specific point, may allow for a faster or easier method as it may be easier for a user to identify a point within a broader region than it is to identify an exact point. The accuracy threshold may be a static value, or may be capable of being updated. In the latter case, the accuracy threshold may be capable of being updated by a user, or by the system. For example, a user may be able to increase or decrease an accuracy threshold using an input to a system, a slider interface on a display, or through other relevant means.

Figure 2:
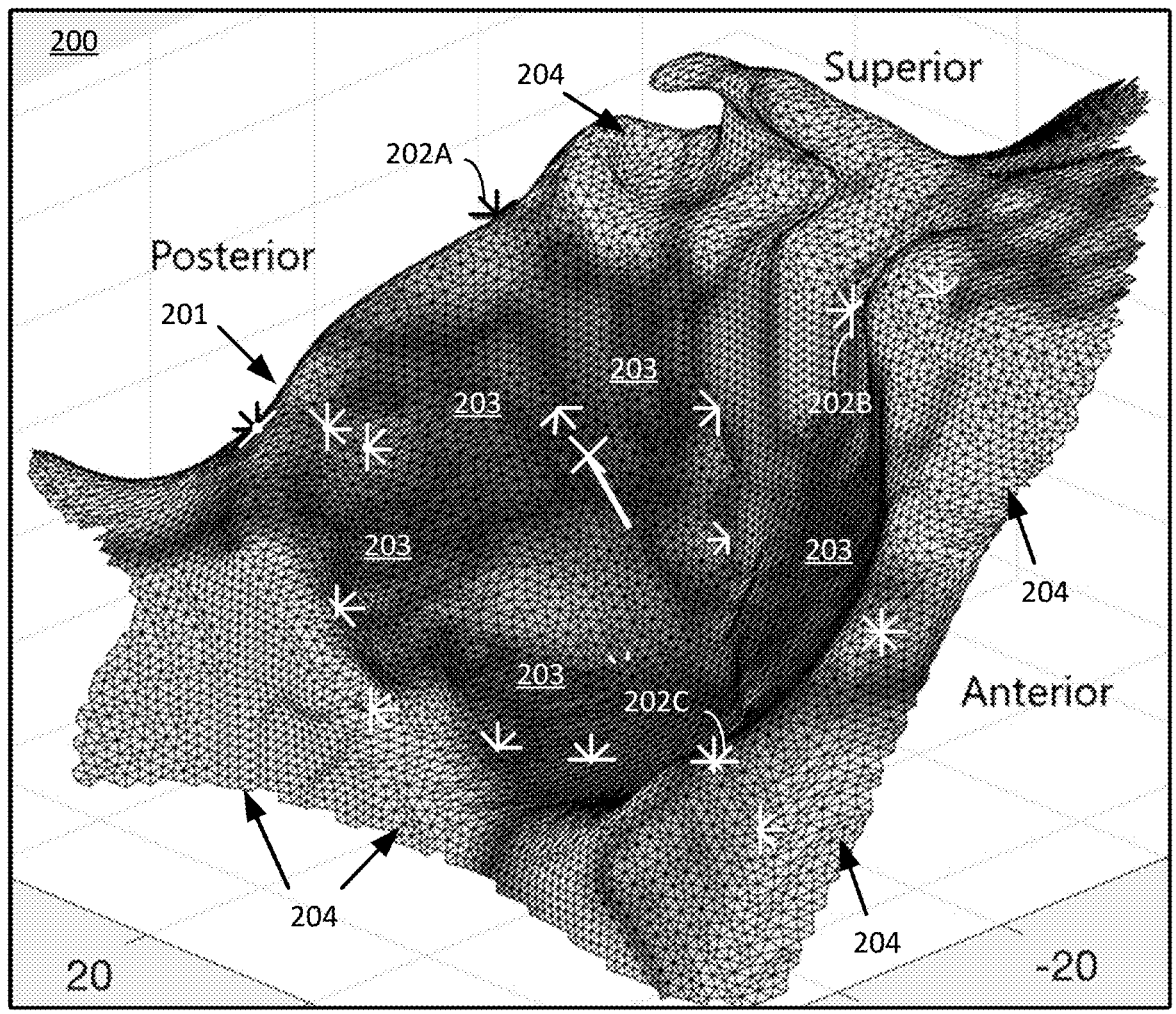
FIGS. 2-3 are simulated screen shots showing respective images generated from a data model during a registration process of a surgical region of a patient anatomy, in different points of view, in accordance with an example.
Figure 3:
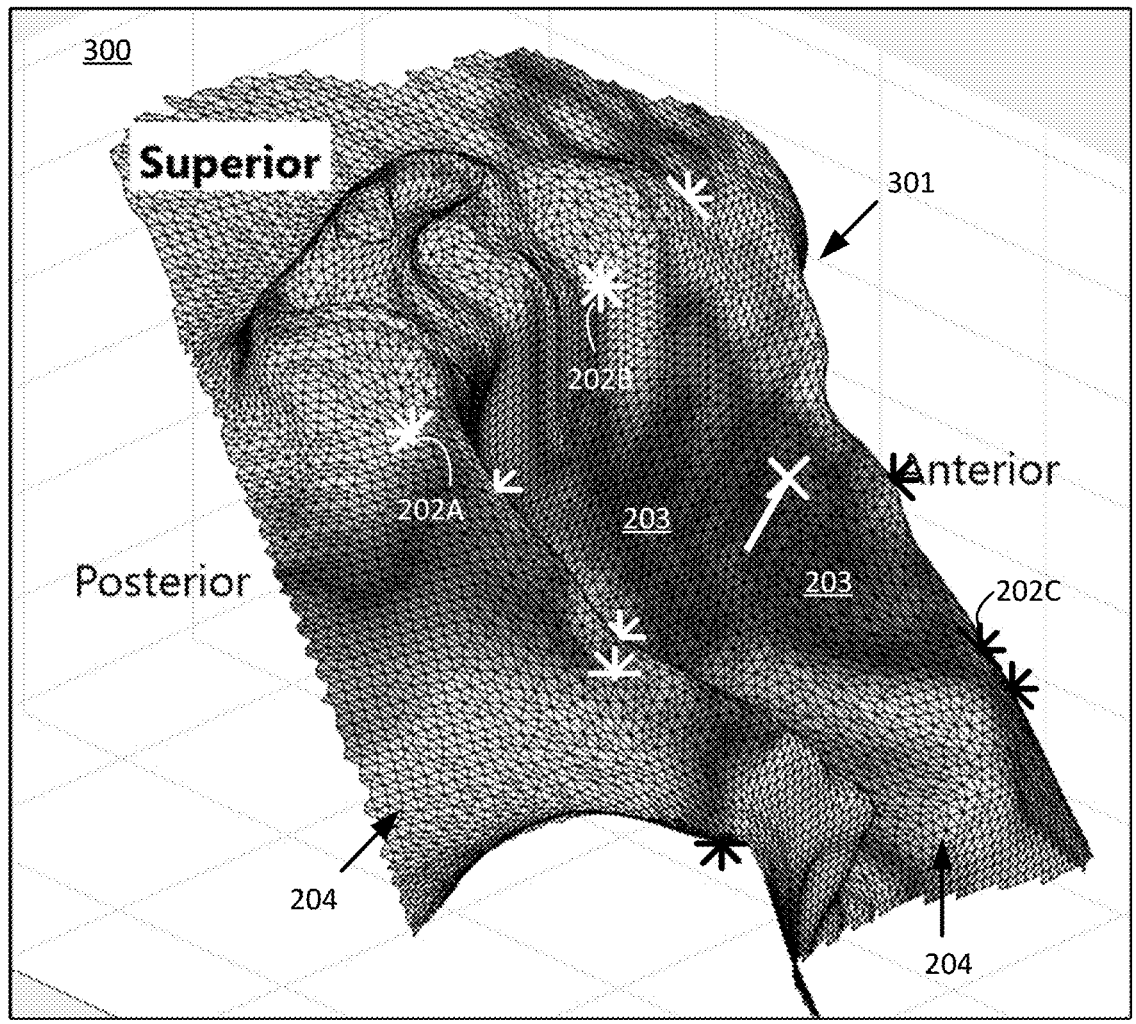

FIGS. 2 and 3 are simulated screen shots 200 and 300 showing respective images 201 and 301 of a surgical region of a patient anatomy, in different points of view, in accordance with an example. The respective images 201 and 301 are generated from a data model (not shown) during a registration process such as described herein. The surgical region in the present example includes an acetabulum of a patient pelvis. Anatomical points (e.g. 202A, 202B, 202C, etc.) received by the processor during the registration process as described herein are illustrated such as by overlaying a graphical element at the location of the anatomical point relative to the data model.

The images 201 and 301 are shown in greyscale herein and in an actual implementation are usually presented in color and more particularly a plurality of colors. Though a shading gradient may be used, different colors are typically used to show a heat map as described herein. Darker regions (e.g. 203) may represent a cooler color such as blue to indicate a region where additional inputting of anatomical points (i.e. from the processor perspective, receiving data responsive to tracking a probe, etc.) will not improve the confidence level and lighter regions (e.g. 204) may represent a warmer color such as yellow to indicate a region where additional inputting of anatomical points will improve the confidence level. Other confidence level indicators (e.g. in various graphical or audible forms) may be provided as described (not shown in FIGS. 2 and 3). Thus FIGS. 2 and 3 show that presenting the representation of the confidence level may comprise displaying a heat map overlaid over one or more regions of an image generated from the digital model, wherein different areas of the heat map identify varying degrees of confidence.

Figure 4:
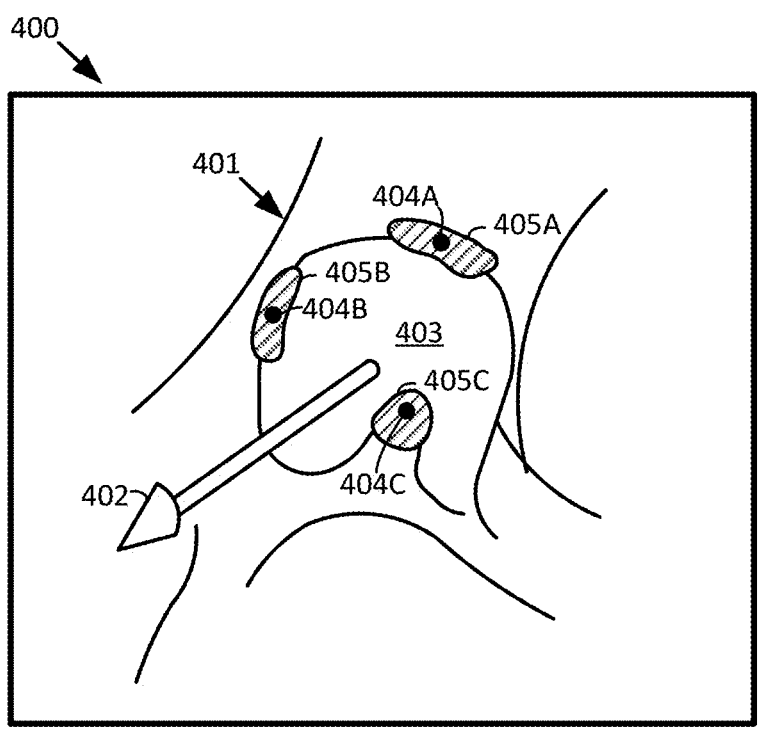
FIG. 4 is a sketch illustration of a screen shot of a graphical user interface in accordance with an example.

FIG. 4 is an sketch illustration of a screen shot 400 of a graphical user interface (GUI) showing an image 401 of a portion of patient anatomy in association with a surgical target position 402 (e.g. as a vector). The portion of patient anatomy includes an acetabulum 403. Also shown in GUI are locations 404A, 404B and 404C. Locations 404A, 404B and 404C have a defined spatial relationship with the surgical target position. About the respective locations 404A, 404B and 404C (where "about" here means "surrounding but not necessarily equally in all directions") are local regions 405A, 405B and 405C determined relative to the locations 404A, 404B and 404C as suggested regions to probe. As noted previously, each local region may be generated by computing the deviation from the surgical target position, by substituting the location with points within the local region, and selecting a region comprising points where the deviation is below an accuracy threshold. More than one option for locations may be offered, for example, in respective sets of locations with each set having a different spatial relationship to the surgical target position 402. Each set of locations may have a respective set of (associated) local regions. A user may choose from among the sets of locations. Each set of locations comprises three or more individual locations.

Additional methods may comprise providing the surgical target location for display relative to the digital model. In one example, the surgical target location may include a graphical representation of: a prosthesis, such as an acetabular component useful in THA; a medical instrument; anatomical structures, such as bones, blood vessels, arteries, veins, nerves; etc.

In one example, the surgical target position may be a plane (or equivalently, a vector perpendicular to the plane). The defined spatial relationship may be, for example, a matching relationship (i.e. the 3 or more locations on the digital model form a plane that matches the surgical target position).

In one or more methods, which may be implemented in part by a system such as one or more of those described herein, the defined spatial relationship may be a pose in a known coordinate system, such as an anatomical coordinate system.

A method may further comprise: receiving pose data of actual locations on the patient's anatomy corresponding to the locations on the digital model from an input system, which may include a localization system. The method may then include determining the surgical target position with respect to the localization system's coordinate frame based on the pose data and the defined spatial relationship. The system may then provide navigational information with respect to the surgical target position.

In an example, such a method may further comprise registering the anatomical coordinate system to the localization system. In such an example, the defined spatial relationship may be a pose with respect to the anatomical coordinate system. The pose may be provided as an input to the localization system, to clarify the relative position of the surgical target position and the anatomical coordinate system.

Figure 5:
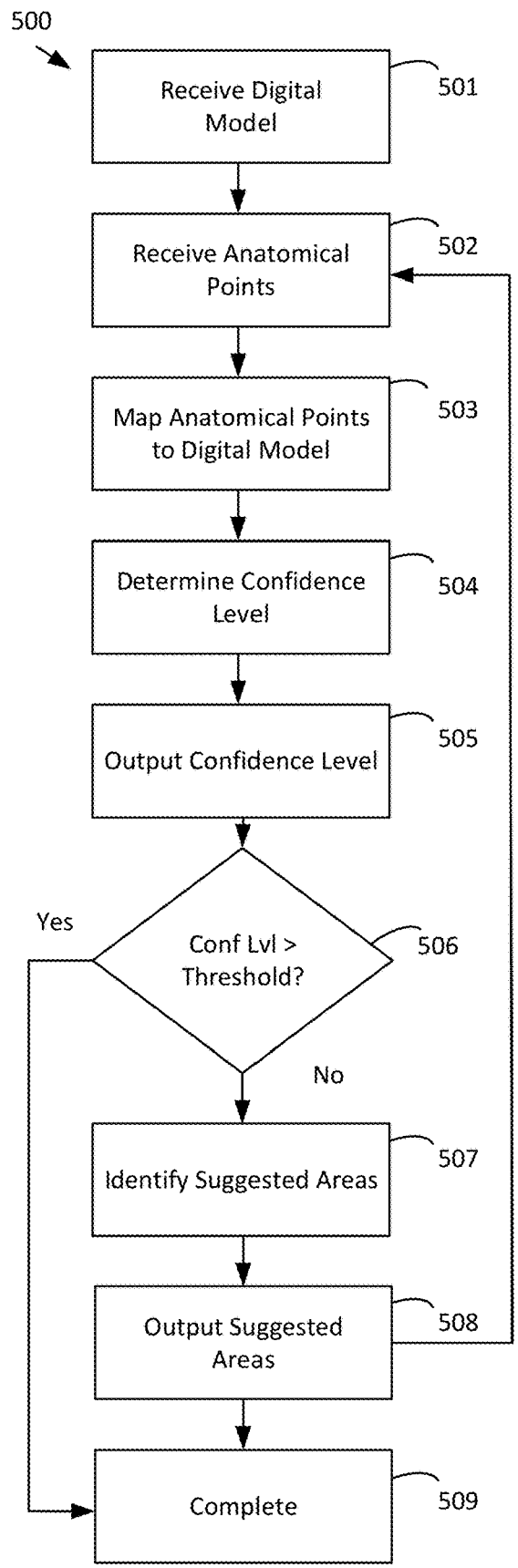
FIGS. 5-7 are flowcharts of example operations of a computer system as described herein.

FIG. 5 is a flowchart illustrating operations 500 which may be implemented by one or more systems defined herein. At step 501, a computer system (e.g. a processor thereof) receives a digital model representative of a surgical region of a patient anatomy. The digital model may be a three-dimensional digital model (e.g. based on a segmented CT or MRI Scan, an EOS 3D reconstruction, etc.) At step 502, the system receives a plurality of anatomical points, the anatomical points indicating actual points on the surgical region of the patient anatomy. The anatomical points may be received from an input system, such as a vision system configured to determine the position of a tip of a probe, a laser scanning system, etc. At step 503, the system maps the anatomical points to the digital model, in an attempt to determine a correlation between the digital model and the patient. The system, as shown at step 504, will determine a confidence level associated with the mapping of the anatomical points to the digital model. The confidence level may indicate the likelihood that the system has correctly correlated the received anatomical points to the digital model. The system may then, at step 505, display the confidence level to the user. The confidence level may be displayed to the user on a screen that shows a numerical confidence value, such as a percentage, or the confidence level may be displayed as a heat map, which illustrated graphically the confidence level in one or more areas of the digital model. For example, if all the anatomical points are provisionally mapped to one area of the digital model, the heat map may be localized around that area. In another example, if there are multiple areas of the digital model where there are potential fits for mapping the anatomical points, there may confidence levels shown for each of those areas. In another example, the system may simply display a "yes/no" type indication to a user, indicating that the system is, or is not, satisfied with the mapping. As shown at step 506, if the determined confidence level exceeds a predetermined confidence threshold, the present method may end. That is, once the confidence level is sufficiently high, there may be no need to continue to receive and map additional anatomical points, and the surgery may progress to a next stage. If the confidence level is below the threshold, the system may identify, as shown at step 507, areas of the patient anatomy to suggest for subsequent anatomical points. For example, the system may identify areas for probing or for scanning which are likely to have the greatest effect on the confidence level with the fewest points. The identification of the areas may be performed as follows.

As before, the function $f(x)$ can represent the mapping of a plurality of anatomical points to a digital model for a given transformation x. If a minimization is not well-constrained, as defined above, then there exist one or more local minima which are close in residual to the global minimum. Since the optimization space represents a transformation space, the different local minima can be represented as relative transformations between each other. That is, if there is a transformation $x_1$ which is one local minimum, and a second transformation $x_2$, that is a second local minimum, there exists a relative transformation $\Delta x$ between these two local minima.

The plurality of anatomical points can be represented by the set of features S, and the digital model can be represented as a set of features P. It is known that $S \in P$. The mapping function $f(x)$ applies the transformation x to S, and returns the points $Q \in P$ which are mapped to the transformed S, and a quality for each of these features. The problem of multiple local minimum can be expressed as the fact that the quality of the features mapped with $f(x_1)$ is similar to the quality of points mapped with $f(x_1+x)$, and that the quality of both sets of features is under some threshold.

Since $S \in P$, but can be mapped well to P under multiple transformations, it is desirable to add features to S which would only be mapped well to P under one of the transformations. To accomplish this, the mapping function applies the relative transformation $\Delta x$ to P, and maps it to the original set of features P. The subset of Q with low quality represent the features in P which are most affected by $\Delta x$. These features can be suggested to the user as features to add to S, which would help those features to only map to P under a single transformation.

The areas to suggest may be chosen in part based on the precision required to obtain additional anatomical points from the region. For example, providing a region of interest, as opposed to specific points of interest, requires less precision from a user and thus makes the system easier to use. On the other hand, identifying exact points for a user to probe may require significant precision on the part of the user, may be more prone to error, and may require the identification of significantly more points before a desired confidence level can be reached.

After identifying the areas to suggest, at step 508 the suggested areas may be displayed to a user. The suggested points may be displayed to a user in a number of ways, such as one or more specific digital points overlaid on the digital model, or through a heat map. The heat map may be the same heat map displayed to the user to illustrate the confidence level, or may be a different heat map. The heat map may indicate one or more areas to the user, and may indicate points or regions. In one example, the system may omit the step of displaying the confidence level, and instead only display the suggested points or regions. The system may subsequently receive additional anatomical points from a user.

Figure 6:
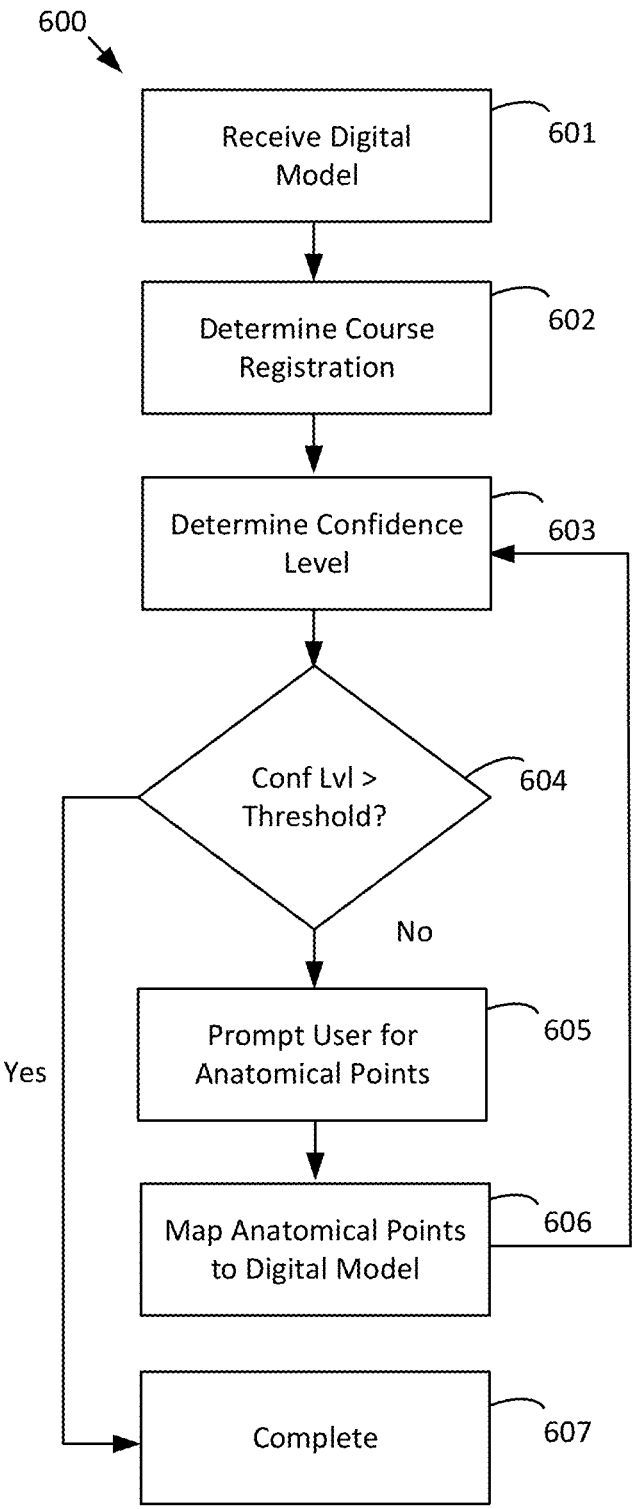

FIG. 6 is a flowchart illustrating operations 600 which may be implemented by one or more systems defined herein. A processor of a computer system is shown receiving, at step 601, a digital model, which comprises a three-dimensional representation of a patient anatomy. At step 602, the system determines a coarse registration of a patient anatomy relative to the digital model. Determining a coarse registration may comprise determining a plurality of digital points, or digital regions, on the digital model to suggest that a user identify, such as through an input system. For example, a system may identify a plurality of regions around an acetabulum, an ischial tuberosity, or other area which may be identified on the digital model, and which a user may be able to identify on the patient anatomy. The user may then identify anatomical points corresponding with the digital points or regions, such as through scanning or probing the region. The coarse registration may be determined with as few as three points, but more anatomical points may also be used to improve the registration. At step 603, the system may determine a confidence level related to the correlation of the coarse registration to the digital model. At step 604, the system may determine whether the confidence level has reached a predetermined threshold confidence level. If the confidence level is at or above the threshold level, via a Yes branch, the system may then be complete at step 607, at which point a surgery may progress to a next step. If the confidence level has not yet reached the threshold confidence level, via a No branch, the system may then prompt a user to input one or more additional anatomical points, at step 605, using an input system. The system may also provide suggestions to the user as to anatomical points or regions from which the user should obtain the additional anatomical points, such as by identifying digital points or digital regions on the digital model. After receiving one or more anatomical points, at step 606, the system may then update the registration using the received anatomical points, and the system returns to step 603 to determine an updated confidence level. The process may then continue in this manner until the confidence level reaches or exceeds the threshold.

Figure 7:
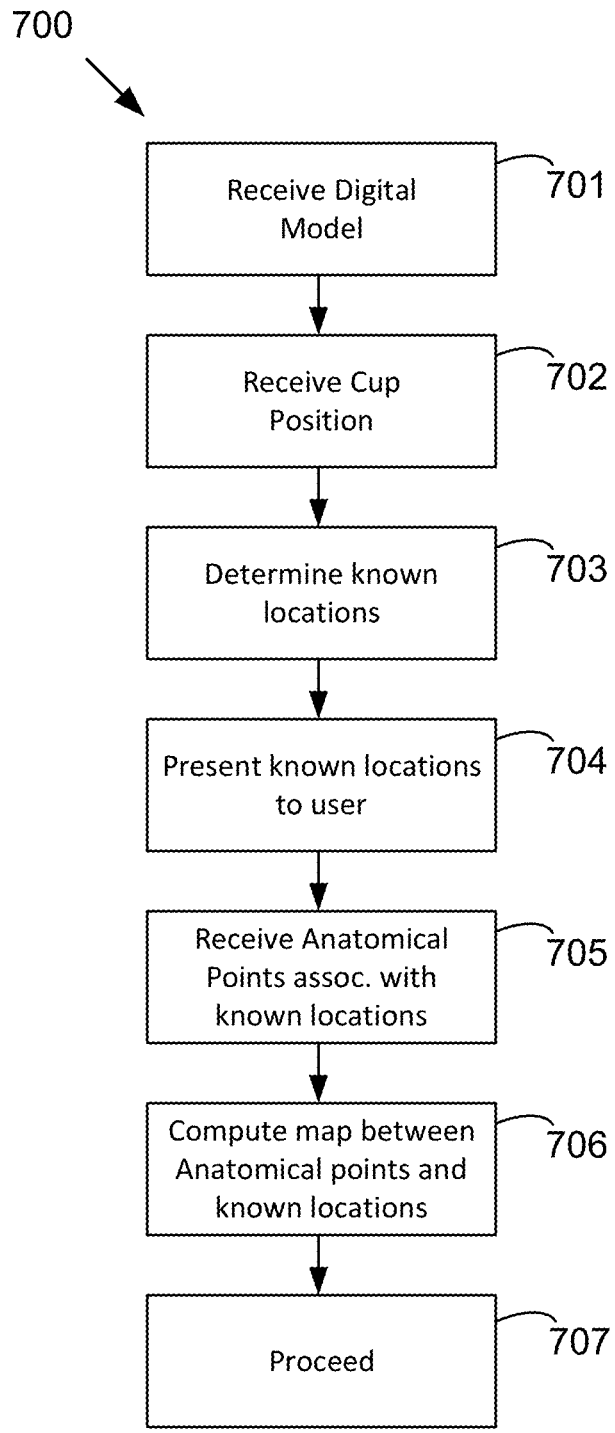

FIG. 7 is a flowchart showing operations 700 which may be performed by a computer system as described herein. Operations 700 illustrate a process of using a digital model and a surgical target position during a surgical procedure. The process may be useful, for example, in planning a cup position during a THA procedure. At step 701, a digital model is obtained (e.g. by the processor of the computer system). The digital model may be any three-dimensional model (e.g. based on a CT scan, an MRI, an EOS scan, etc.) At step 702, the system (e.g. the processor) receives a surgical target. The surgical target may comprise one or more numerical values, such as a cup angle, inclination, anteversion, offset, etc., which may be useful during the placement of an acetabular cup prosthesis a THA. The surgical target may be received, for example, from a user entering data into the system. In another example, the surgical target may be received from surgical planning software (e.g. via a communication or retrieved from a storage unit, etc.)

At step 703, the system determines locations on the digital model (referred to herein as "known locations") to provide to the user for identification on the patient anatomy. The known locations may be determined based on their position, geometry, uniqueness, or other criteria which may make them identifiable by a user. At step 704, these known locations are presented to a user. At step 705, the system receives anatomical points associated with the known locations, and determines the location of the anatomical points in three-dimensional space. The anatomical points may be received by a user probing the areas corresponding to the known locations, through scanning, or through other suitable methods.

At step 706, the system computes a mapping between the known locations and the associated anatomical points. The computation may include determining a transform function configured to transform points in a first reference frame, or first reference axes, to points in a second reference frame or reference axes. That is, the transform function may allow the translation of coordinates in a three-dimensional space relative to the anatomical points to be transformed to coordinates relative to the digital model. In one example, this may include determining a surgical target position with respect to a localization system's coordinate frame based on pose data and a defined spatial relationship. Once the mapping has been performed, the system then progresses to the next step of a surgical procedure, as shown at step 707. The next step of the procedure includes providing navigational information with respect to the surgical target position. For example, the next step of the navigational procedure may include determining the location and position of a prosthesis, such as an acetabular cup prosthesis, in real time during a surgical procedure. The determination of the prosthesis position may include using a vision system to monitor the position of the prosthesis and/or a medical instrument attached to a prosthesis.

A system configured to implement the steps of FIG. 7 may comprise one or more computer systems, configured to implement aspects of the method. For example, a system may comprise a first computer configured to receive the digital model and the target cup position, to determine the known locations, and to present the locations to a user. A second computer may be configured to receive the anatomical points associated with the known locations, to compute the mapping between the anatomical points and the known locations. Step 707 may then be performed using one of the first computer or second computer, or could use another computer altogether.

Figure 8:
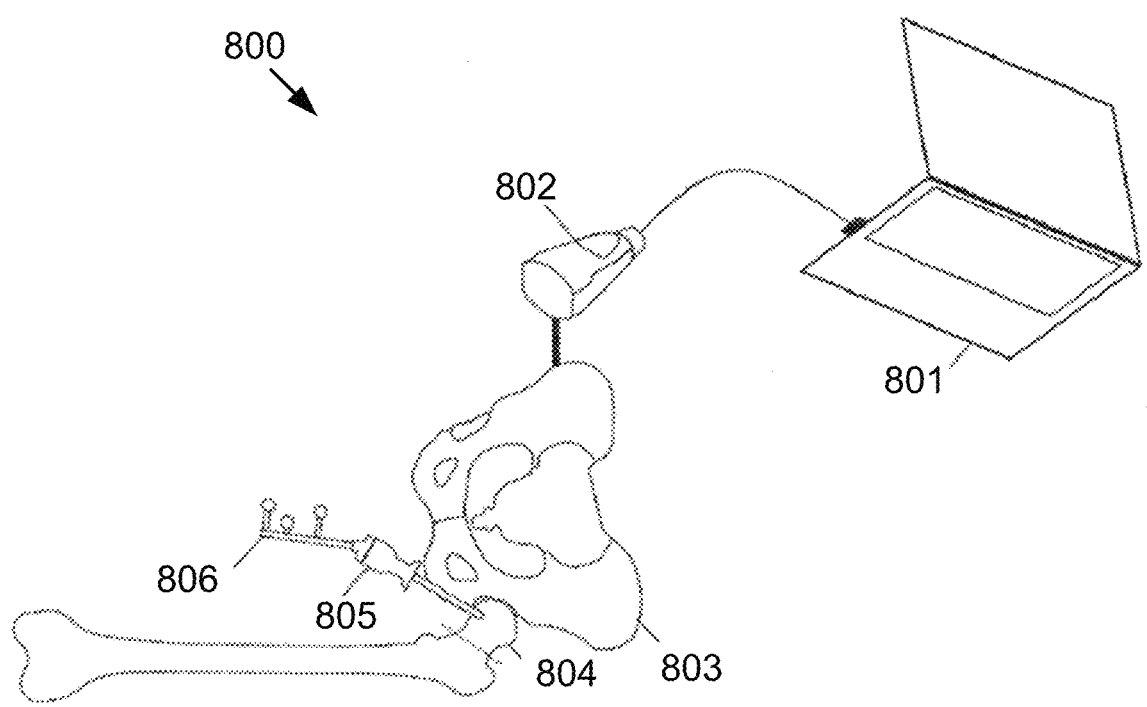
FIG. 8 is an illustration of a computer system for surgical planning and/or surgical navigation relative to an anatomy of a patient in accordance with an example.

FIG. 8 illustrates an exemplary system 800 comprising an input system comprising, in this example, a camera 802 configured to monitor the position of a plurality of spheres at the end 806 of a probe 805, the probe having a tip at the end opposite the spheres. The camera 802 is configured to provide data representative of the position of the plurality of spheres to a computer 801. The illustrated computer 801 includes an integrated display device but may be coupled to a separate (standalone) display device such as a computer monitor. Other display devices may include goggles/glasses for a heads up or virtual reality type display. The display device may be touch or other gesture-enabled (e.g. via a camera or motion sensors). The computer may have or be coupled to a microphone to receive voice commands and have or be coupled to a speaker to output sound which may be natural language output such as via a computer generated voice.

In the present example, the camera 802 and the computer 801 are configured to communicate through a wired connection. The probe 805 may be used to identify the location of a portion of a patient anatomy, such as a femoral head 804, a pelvis 803, etc.

Any of the computing systems or devices described herein may comprise a processing unit with one or more processors, memory coupled to the processing unit storing instructions to configure the execution of the processors. The computing unit may have or be coupled to input, output and/or input/output devices and systems. The computing unit may have or be coupled to other storage devices (i.e. other than memory). Storage devices may take different forms and/or configurations, for example, as short-term memory or long-term memory. Storage devices may be configured for short-term storage of information as volatile memory, which does not retain stored contents when power is removed. Volatile memory examples include random access memory (RAM), dynamic random access memory (DRAM), static random access memory (SRAM), etc. Storage devices, in some examples, also include one or more computer-readable storage media, for example, to store larger amounts of information than volatile memory and/or to store such information for long term, retaining information when power is removed. Non-volatile memory examples include magnetic hard discs, optical discs, floppy discs, flash memories, or forms of electrically programmable memory (EPROM) or electrically erasable and programmable (EEPROM) memory. Though shown as a laptop configuration, other configurations may be employed such as a personal computer, workstation, etc.

The computing unit may have a communication system for communicating with other devices or systems or internally. The communications capabilities may include one or more wireless or wired capabilities. The features and operations herein may be implemented in software, hardware of combinations thereof. Software comprising instructions (e.g. Computer program code) for carrying out operations when executed by the processor may be written in any combination of one or more programming languages, e.g., an object oriented programming language such as Java, Smalltalk, C++ or the like, or a conventional procedural programming language, such as the "C" programming language or similar programming languages.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What we claim is:

1. A computer implemented method for a surgical procedure comprising:
   receiving a digital model identifying at least a portion of a bony structure of a patient anatomy;
   receiving a plurality of anatomical points identifying actual locations on the patient anatomy;
   creating a mapping by correlating the plurality of anatomical points to the digital model, wherein the mapping matches the received anatomical points with a surface of the bony structure identified in the digital model;
   determining a confidence level corresponding to a likely correctness of the mapping of the anatomical points to the digital model;
   presenting a representation of the confidence level;
   determining, from the digital model, the anatomical points, and the confidence level, suggested regions from which to obtain additional anatomical points to increase the confidence level of the mapping;
   presenting the suggested regions;
   receiving one or more additional anatomical points from at least one of the suggested regions;
   updating the mapping by correlating at least a subset of the plurality of anatomical points and the one or more additional anatomical points to the digital model; and
   updating the confidence level for the mapping as updated, wherein the confidence level is updated in at least near real time when an additional anatomical point used in the updated mapping is received.

2. The method of claim 1 wherein receiving the plurality of anatomical points comprises determining a location of a tip of a probe for each of the plurality of anatomical points.

3. The method of claim 1 wherein receiving the plurality of anatomical points comprises receiving input from a scanner being manipulated to scan a region of the patient anatomy.

4. The method of claim 1 wherein the representation of the confidence level comprises one or more of a numerical value, a binary value, or a heat map.

5. The method of claim 4 wherein presenting the representation of the confidence level comprises displaying a heat map overlaid over one or more regions of an image generated from the digital model, wherein different areas of the heat map identify varying degrees of confidence.

6. The method of claim 4 wherein the binary value identifies whether the confidence level has reached a predetermined threshold value.

7. The method of claim 1 wherein the presenting the suggested regions comprises presenting a heat map overlaid on a visualization of the digital model wherein the heat map indicates the suggested regions.

8. The method of claim 7, wherein the suggested regions are determined, at least in part, to provide an area from which the additional anatomical points can be obtained which will increase the confidence level without requiring a high degree of precision to indicate the additional anatomical points.

9. The method of claim 1, wherein the suggested regions are defined to increase the confidence level through an addition of a minimal number of additional anatomical points.

10. The method of claim 9, wherein each of the suggested regions is determined from areas of the patient anatomy which are physically unique, relative to nearby areas of the patient anatomy, the areas that are physically unique being distinguishable by fewer anatomical points relative to the nearby areas.

11. The method of claim 1, wherein the confidence level is determined from an optimization residual resulting from an optimization computation that determines the mapping.

12. The method of claim 1, wherein the confidence level is updated in at least near real time when the additional anatomical point is received and without receiving one or more points provided to verify or validate the mapping.

13. The method of claim 9, further comprising presenting a notification in response to the confidence level as updated in at least near real-time reaching a goal or target confidence level indicating to cease providing the additional anatomical points.

14. A system for performing patient registration during a medical procedure, comprising:
    a computer system;
    a data store;
    an input system; and
    a display system;
    wherein the computer system is configured to:
        receive a digital model representative of a patient anatomy;
        receive, from the input system, information identifying a plurality of anatomical points, the anatomical points corresponding to a location of a patient in three-dimensional space;
        determine a mapping to map the plurality of anatomical points to digital points on the digital model;
        determine a confidence level associated with the mapping; and
        determine, from the digital model, the anatomical points, and the confidence level, one or more suggested areas of a patient anatomy from which to obtain additional anatomical points to increase the confidence level of the mapping;
        presenting the one or more suggested regions;
        update the mapping by correlating to the digital model at least a subset of the plurality of anatomical points and one or more additional anatomical points as received for at least one of the suggested regions; and
        update the confidence level for the mapping as updated, wherein the confidence level is updated in at least near real time when an additional anatomical point used in the updated mapping is received.

15. The system of claim 14, wherein the computer system is further configured to output, via the display system, a representation of the confidence level associated with the mapping.

16. The system of claim 14, wherein the computer system is configured to output to the display system a heat map in association with an image generated from the digital model, wherein the heat map indicates the suggested areas of the patient anatomy from which the additional anatomical points are to be received to improve the confidence level.

17. The system of claim 16 wherein the computer system is further configured to receive additional information representative of the additional anatomical points to update the confidence level and to update the heat map.

18. The system of claim 14 wherein the input system comprises a vision system and a probe, wherein the vision system is configured to view at least a portion of the probe and to determine, based on a geometry of the probe, a position of the probe in three-dimensional space.

19. The system of claim 14 wherein the computer system is further configured to:
    receive an initial coarse patient registration correlating the location of the patient in three-dimensional space with the digital model; and
    determine an initial confidence level and the one or more suggested areas based on the initial coarse patient registration.

20. The system of claim 14, wherein the suggested regions are defined to increase the confidence level through an addition of a minimal number of additional anatomical points.

21. The system of claim 14, wherein the confidence level is updated in at least near real time when an additional anatomical point is received and without receiving one or more points provided to verify or validate the mapping.

22. The system of claim 21, wherein the computer system is further configured to present a notification in response to the confidence level reaching a target confidence level, the notification indicating to cease providing the additional anatomical points.

* * * * *